United States Patent [19]

Falcetta et al.

[11] Patent Number: 4,633,003
[45] Date of Patent: Dec. 30, 1986

[54] SILOXANE MONOMERS FOR OPHTHALMIC APPLICATIONS

[75] Inventors: Joseph J. Falcetta; Joonsup Park, both of Arlington, Tex.

[73] Assignee: Alcon Laboratories, Inc., Fort Worth, Tex.

[21] Appl. No.: 801,259

[22] Filed: Nov. 25, 1985

[51] Int. Cl.$^4$ ............................ C07F 7/08; C07F 7/10
[52] U.S. Cl. ...................... 556/419; 556/421; 556/440; 528/32; 526/279; 351/160 H; 351/160 R
[58] Field of Search ................ 556/440, 419, 421

[56] References Cited

U.S. PATENT DOCUMENTS

| Re. 31,406 | 10/1983 | Gaylord | 526/279 |
|---|---|---|---|
| 3,808,178 | 4/1974 | Gaylord | 556/440 X |
| 4,120,570 | 10/1978 | Gaylord | 556/440 X |
| 4,139,548 | 2/1979 | Tanaka et al. | 260/448.2 B |
| 4,152,508 | 5/1979 | Ellis et al. | 526/279 |
| 4,153,641 | 5/1979 | Deichert et al. | 260/827 |
| 4,276,402 | 6/1981 | Chromecek et al. | 556/419 X |
| 4,294,974 | 10/1981 | Le Boeuf | 556/440 |
| 4,306,042 | 12/1981 | Neefe | 556/440 UX |
| 4,314,068 | 2/1982 | Novicky | 556/440 |
| 4,327,203 | 4/1982 | Deichert et al. | 526/279 |
| 4,424,328 | 3/1984 | Ellis | 526/279 |
| 4,450,264 | 5/1984 | Cho | 526/279 |
| 4,543,398 | 9/1985 | Bany et al. | 556/419 X |
| 4,545,980 | 10/1985 | Hill | 556/440 X |

FOREIGN PATENT DOCUMENTS

| 1210845 | 2/1966 | Fed. Rep. of Germany | 556/440 UX |
| 59-86612 | 5/1984 | Japan | 556/440 UX |

Primary Examiner—Paul F. Shaver
Attorney, Agent, or Firm—James A. Arno; Gregg C. Brown

[57] ABSTRACT

Novel colorless siloxane monomers containing both an aromatic ring and vinyl functionality are employed as a monomer for preparing copolymers that are ophthalmically useful. The monomer has good oxygen permeability, allows preparation of copolymers that have good machineability, and is easily wettable. Moreover, because of its compatability with other copolymers it can be useful to make a wide variety of types of lenses including hard and soft, and ocular implants as well.

8 Claims, No Drawings

SILOXANE MONOMERS FOR OPHTHALMIC APPLICATIONS

BACKGROUND OF THE INVENTION

The present invention relates to a class of novel siloxane monomers containing both an aromatic ring and vinyl functionality. Polymers comprising variable amounts of these monomers are transparent to visible light, have a high refractive index, and are useful, inter alia in fabricating lenses, especially contact lenses and intracameral devices such as corneal inserts and intraocular lenses. Contact lenses generally are fillerless, oxygen transportable, hydrolytically stable, biologically inert, transparent plastic bodies which are prepared from polymerization, or copolymerization of monomers. This invention describes a new monomer, which is a siloxane monomer containing both an aromatic ring and vinyl functionality.

The polymers and copolymers described herein can be usefully employed for making "hard" or "soft" contact lenses, intraocular implants, intracorneal implants, semisoft contact lenses, as well as in other biomedical applications. Importantly, the polymers of this invention, when properly copolymerized with other materials have wide adaptability and compatability with other monomers. They are therefore versatile and can be adapted to prepare good hard lenses, as well as good soft lenses. They may also have other uses such as permeable films, etc., but the primary description given will emphasize the lens utility.

Hard contact lenses have the advantages of excellent machinability, excellent stability, and excellent visual clarity. However, hard contact lenses have their disadvantages, as well. Generally for many, including the most common hard lenses, i.e. those made of polymethyl methacrylate (PMMA), oxygen permeability is low and the hydrophilic properties are poor.

It is important and essential that the cornea have access to atmospheric oxygen in order that an oxygen-carbon dioxide exchange can occur. Put another way, without constant eye exposure to the atmosphere, a state of oxygen edema can occur within the eye, which is potentially capable of causing damage. Thus, hard contact lenses, while having many practical advantages, generally are not altogether satisfactory because they most often have poor oxygen permeability.

A good hard contact lens would have not only excellent oxygen permeability, but also excellent tear-fluid wettability. Wettability is important in that if the lens is not wettable it cannot be comfortably worn in the eye. The patient will perceive the lens as uncomfortable and scratchy, absent good wettability.

Recently soft contact lenses have captured a significant market share. However, soft contact lenses are also not without disadvantages. Soft contact lenses generally have excellent oxygen permeability, and excellent eye comfort. However, soft lenses also readily attract and accumulate foreign debris, necessitating frequent cleaning. Accordingly, both soft lenses and hard lenses, including gas permeable hard lenses, have their respective advantages and disadvantages.

Generally, in the past, polymer formulation for optical lens products has involved an initial determination as to whether one was formulating either a hard lens or a soft lens, followed by formula manipulation within a distinctly different class of monomers useful for one type, but not necessarily useful for the other. The monomers of the present invention, however, can be used for making either hard or soft lenses.

Indeed, it is an object of the present invention to provide a novel class of siloxane monomers characterized by containing both an aromatic ring functionality and vinyl functionality at certain stereo-directing positions, which can be employed as a monomer for preparing copolymers useful as materials for making a wide variety of types of optical products including hard lenses, soft lenses, and ocular implants.

A further object of the invention is to provide a monomer of the type specifically mentioned above which is not only of good oxygen permeability, but which is highly compatible with other monomers, and which, when copolymerized with other monomers provides wettability, without sacrificing oxygen permeability.

A still further object of the present invention is to provide hard gas permeable contact lenses which contain as a monomer of variable presence, the hereinafter defined class of monomers of the present invention.

A further object of the present invention is to provide soft contact lens of the hydrogel type which contain as a monomer of variable presence, the hereinafter defined monomer of the present invention.

A further object of the present invention is to provide a copolymerizable compound suited for preparing contact lenses which have good oxygen permeability, are machineable, and which can be used selectively for either hard or soft lenses, and which can be comfortably worn.

A still further object of the present invention is to prepare a monomer which can be copolymerized to provide a copolymer useful for optical products, particularly gas permeable hard contact lenses, wherein the copolymer has a DK, i.e. oxygen permeability constant value within the range of from about 12 to about 70, and which also has a highly wettable surface. Such lenses are comfortable, when worn show no evidence of substantial corneal edema, are of good machineability, are dimensionally stable, are tear wettable, and as well have suitable lipidic properties to optimally interact with tear fluid.

The method and means of accomplishing each of the above objectives, as well as others will become apparent from the detailed description of the invention which will follow hereinafter.

SUMMARY OF THE INVENTION

Certain siloxane monomers which contain both an aromatic ring and vinyl functionality are provided. The siloxane monomers can be used as a main monomer ingredient in providing copolymers useful for making either hard or soft contact lenses, or other optical products. The new siloxane monomers of the present invention provide excellent oxygen permeability in copolymers, without adversely impacting on other desirable properties such as machineability, wettability, lipophilicity, and dimensional stability. Moreover, a polymer, and copolymers containing it, are useful for making lenses which are substantially inert to the eye and transparent, and provide good visual clarity and sharpness of image. Such objectives are accomplished by a unique combination of functional groups in the monomer, selectively stereo-positioned on the monomer. In one preferred soft lens embodiment, the monomer of the present invention appears to have special properties in terms of its compatability with hydrogel forming monomers such as hydroxyethyl methacrylate (HEMA).

DETAILED DESCRIPTION OF THE INVENTION

It has now been found that the above-mentioned objects, as well as others, can be obtained by a monomer compound containing both an aromatic ring and vinyl functionality, having the following formula (I):

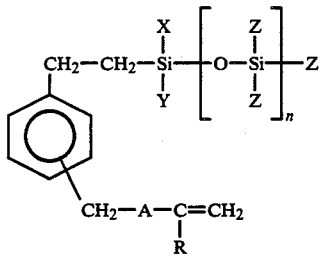

where
(1) "A" is selected from the group consisting of:

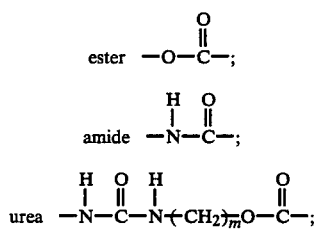

where m is a number and is from 2–4;
(2) R is hydrogen or methyl;
(3) X and Y are selected from the group consisting of $C_1$ to $C_5$ alkyl groups, phenyl groups and W groups;
(4) W is a group of the structure

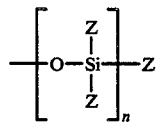

(5) Z is selected from the group consisting of $C_1$ to $C_5$ alkyl groups and phenyl groups; and
(6) n is an integer from zero to five.

It is not known precisely why the monomer of the present invention has a wide range of other monomer compatability, allowing it to be useful in making either hard or soft contact lenses, but it does. Without being bound to any theory, it is believed that perhaps its wide compatability is achieved because within the structure there is a synergistic relationship between the unique combination of functional groups and their spatial relationship to each other, giving the desirable properties. It is believed the presence of the aromatic ring contributes to a desirably higher index of refraction, on the order of 1.4515; the presence of the siloxane moiety provides for oxygen permeability; and, the presence of the vinyl functionality provides for good overall polymerization properties, without adversely impacting other desirable properties, especially oxygen permeability. In some instances where "A" in formula [I] is a urea derivative, the urea functionality provides for special desirability in preparing compatable hydrogel type lenses.

The novel monomers of the present invention are representatively prepared according to the following synthetic scheme, starting with chloromethyl styrene.

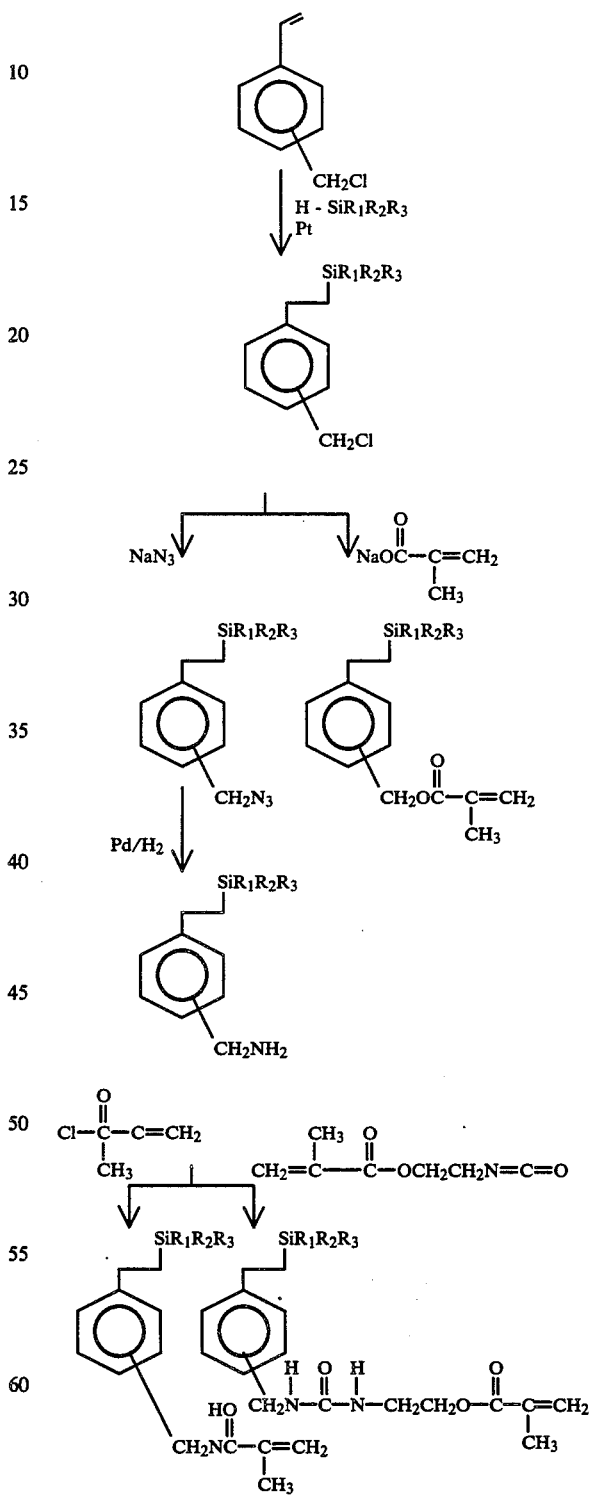

The reaction depicted in the above presented synthetic scheme are all generally known types of reactions, and include the following steps. The chloromethylstyrene, which is commercially available from, for example, Dow Chemical Company as a 60:40 mixture of meta and para is reacted with a siloxane in a hydrosilation reaction, catalyzed by platinum to provide siloxane functionality. The temperature and reaction time are typical of hydrosilation and generally are from about 40° C. to about 150° C., preferably at 80° C. for from about four hours to about eight hours. The siloxanes are available from numerous sources including Petrarch Systems, Inc. of Bristol, Pa.

After the hydrosilation, assuming one desires to provide ester functionality for "A" the scheme represented by the right hand branch of the synthesis flow sheet is followed. In particular, as depicted the siloxane is reacted with sodium methacrylate in a classic nucleophilic displacement reaction at from about 80° C. to about 140° C. for from 0.5 hours to 3.0 hours to give the desired ester monomer of this invention.

If, on the other hand, one desires to prepare the amide or urea monomers of this invention the reaction scheme depicted on the left hand branch of the synthesis flow sheet is followed. To prepare the amine, the siloxane is reacted with sodium azide, followed by palladium promoted reduction, or in other words, hydrogenation. The azide reaction is conducted at 60° C. for from about 2.0 hours to about 6.0 hours and the hydrogenation for from 0.5 hours to about 2.0 hours, preferably from 0.5 hours to 1.0 hours at from 0° C. to 40° C. The amine compound of the present invention is the product.

If one desired to form the amide compound, the amine is reacted with an acid chloride to undergo classic amidation. The reaction is exothermic and typically run below room temperature, preferably at about 0° C. for from about 0.20 hours to about 1.0 hours.

Finally, if one desired a ureido compound, the amine is reacted with an isocyanate to yield the desired ureido compound of the invention. The reaction is run for about 0.20 hours to 1.0 hours at below room temperature, preferably about 0° C.

Unless otherwise stated, at least equimolar quantities of the reactants are employed. Other conditions and specifics of the reaction condition will become apparent from the examples below.

The monomer of the present invention can be successfully employed as a monomer for preparing copolymers useful as a transparent material for contact lenses. When the compound of the invention is copolymerized with other particular comonomers, such as a hydrophilic comonomer, there can be obtained copolymers suitable for use with contact lenses which have excellent oxygen permeability, affinity for the cornea, and can be continuously worn, long term, without giving a foreign body sensation. For instance, when from about 25% by weight to about 50% by weight formula [I] monomer of this invention is copolymerized with from about 10% by weight to about 40% by weight of a comonomer fluorohydroxyalkylstyrene compound which also improves wettability, from about 0% by weight to about 40% by weight of a monomer compatible mechanical property modifier such as methyl methacrylate, tertiary butyl styrene or cyclohexyl methacrylate, from about 0% by weight to about 5% by weight of a hydrophilic wetting agent monomer such as methacrylic acid, and from about 0.5% by weight to about 2% by weight of a cross-linker such as ethyleneglycol dimethacrylate, an excellent hard gas permeable contact lens is achieved.

As those skilled in the art know, the copolymerization reactions mentioned herein typically occur in the presence of a radical polymerization initiator such as azobisisobutyronitrile or azobisdimethylvaleronitrile by means of a bulk polymerization reaction.

Generally, characterization of the lens as hard or soft will depend upon the comonomer, polymerized with the formula [I] monomers of the present invention. Other hydrophilic comonomers which may be incorporated to provide increased wettability, are those fluorohydroxyalkylstyrenes previously mentioned. Other comonomers useful for making hydrogel type soft lenses and hard lenses include the hydroxy alkyl acrylates and methacrylates; hydroxyethyl methacrylate (HEMA), hydroxyethyl acrylate, hydroxy-polyethoxy ethyl methacrylate and the like. Examples of another class of suitable hydrophilic monomers are the N-vinyl heterocyclic monomers, suitable examples of such monomers being N-vinyl-2 pyrrolidone, N-vinyl pyridine and N-vinyl-$\epsilon$-caprolactam. Also another class of hydrophilic monomers are the polymerizable olefinic acids and amides; suitable examples being acrylic acid, methacrylic acid, itaconic acid, fumaric acid, maleic acid, crotonic acid, acrylamide, methacrylamide and N-(1,1-dimethyl-3-oxobutyl acrylamide). Another suitable group of hydrophilic monomers are the lower alkyl vinyl ethers such as methyl and ethyl vinyl ether.

Other compatible mechanical property modifying monomers can be utilized to change the softening temperature and hardness and to improve machineability of the copolymer. Generally, these are somewhat hydrophobic monomers and preferred are the olefinically unsaturated polymerizable monomers with one polymerizable double bond per molecule. Suitable examples of such monomers are the linear or branched $C_1$ to $C_{10}$ alkyl esters of acrylic and methacrylic acid such as methyl acrylate, ethyl acrylate, butyl acrylate, 2-ethylhexyl acrylate, methyl methacrylate, ethyl methacrylate, butyl methacrylate, cyclohexyl methacrylate, 2-ethylhexyl methacrylate, 2-ethoxyethyl methacrylate, and the like monomers. Examples of other suitable hydrophobic monomers useful as compatible mechanical property modifiers are the vinyl ethers such as butyl vinyl ether and vinyl acetate, vinyl chloride, vinyl propionate, isoprene, vinyl carbazole, and styrene monomers other than those defined above for the main monomer which are styrenes, including alkoxy styrenes, e.g., methoxy and ethoxy sytrene, halogenated styrenes, hydroxyalkyl styrenes, alkoxy alkyl styrenes, and polyalkoxyether sytrenes.

As heretofore mentioned, certain ranges of cross-linking monomers may also be employed. These may be used to harden the resulting copolymer or to improve machineability or stability, or both. Examples of suitable cross-linking monomers are divinyl benzene, di- and higher functionality of methacrylates and acrylates such as ethylene glycol dimethacrylate, tetraethylene glycol dimethacrylate, polyethylene glycol dimethacrylate, trimethylol propane trimethylacrylate, pentaerythritol tetramethacrylate, and allyl methacrylate, allyl itaconate, diallyl itaconate, diallyl adipate and methylenebisacrylamide. The foregoing examples of cross-linking monomers are merely illustrative, others may also be used, and all may be used individually, or in combination.

The monomers of this invention [I], may be used as the only monomer in conjunction with the mechanical property modifier, wetting agent and cross-linker, or it may be used with a comonomer. Use with compatible comonomer is perferred and produces the best results.

While preferred polymerized compositions of this invention would include a formula [I] monomer of this invention, and typically one other compatible comonomer, a wetting agent and a cross-linking agent, other minor ingredients may also be added in making suitable bonnets. Such minors include coloring agents, light absorbers, certain other mechanical property modifiers such as plasticizers and the like, so long as those other materials do not adversely effect the desired properties of formula [I] monomer of the invention and lenses made therefrom.

The contact lenses can be formed from the copolymer by any of the conventional lens lathing molding and/or polishing processes. For example, the polymers can be formed into rods which are cut into small cylinders or disks, often referred to as buttons or bonnets, from which the contact lens can be machined.

The wearing comfort of the contact lenses of the gas permeable hard lens type can be enhanced by the use of well-known wetting solutions, cleaners, disinfectant solutions, comfort drops, and the like.

The invention will be further described in connection with the following examples which are given for purposes of illustration and should not be construed as limiting on the invention. All parts and percents referred to herein are on a weight basis.

EXAMPLES

EXAMPLE 1

Synthesis of tris (trimethylsiloxy) silane-m,p-chloromethyl phenylethane

A catalyst solution is prepared by adding, with stirring, 23.8 g. of concentrated sulfuric acid to a solution of 11.6 g. of ethanol in 16.5 ml of distilled water.

To a 500 ml round bottom flask that is situated on an ice batch, a mixture of 43.6 g. (0.33 mole) of trimethylacetoxysilane and 27.4 g. (0.1 mole) of trimethoxysilane-m,p-chloromethyl) phenylethane is added. To this mixture 9.1 ml of the catalyst solution is added in a dropwise manner over a time period of 30 minutes.

The reaction mixture is vigorously stirred for three days at room temperature. After separation, the organic layer is neutralized with sodium bicarbonate, washed with water and dried over magnesium sulfate.

A yield of 31 g. (69.2%) of a slightly yellow liquid having an index of refraction of 1.4515 is obtained at 120°–135° C. (0.3–0.4 mm).

The identity of the compound was confirmed by the infrared spectrum and nmr spectrum [7.1 ppm (m,4H); 0.0 ppm (s,27H)].

EXAMPLE 2

Synthesis of tris (trimethylsiloxy) silane(m,p-methacryloxymethyl)phenylethane

A mixture of 13.4 g. (3.0 mmole) and 3.6 g. (3.3 mmole) of sodium methacrylate in 150 ml of dimethylformamide was stirred at 125° C. for one hour. After cooling with an ice bath, 100 ml of distilled water was added. This reaction mixture was then extracted four times with 100 ml volumes of ethyl acetate. The combined organic layer is washed 3 times with 50 ml of a saturated sodium chloride solution and dried over anhydrous magnesium sulfate. After stripping off the low boiling components by vacuum distillation the final product was obtained at 120°–129° C. (0.1 mm) in a yield of 53.4%.

The identity of the compound was proven by the infrared spectrum and nmr spectrum [7.1 ppm (m,4H), 6.0 and 5.4 ppm (2 broad s,2H), 0.0 ppm (s,27H)].

EXAMPLE 3

Synthesis of tris (pentamethyl disiloxy) silane(m,p-methacryloxymethyl)phenylethane Using a procedure similar to that given in Examples 1 and 2, trimethoxysilane(m,p-chloromethyl)phenylethane was reacted with pentamethylacetoxydisiloxane to form tris (pentamethyl disiloxy)-(m,p-chloromethyl) phenylethane in 44% yield. This compound was then reacted with sodium methacrylate in dimethylformamide solution to give a 83.9% yield of tris (pentamethyl disiloxy) silane-m,p-methacryloyloxymethyl phenylethane.

The identity of the compound was confirmed by the infrared spectrum; 1730 cm$^{-1}$ (C=O), 1640 cm$^{-1}$ (CH$_2$=), 1615 cm$^1$ (aromatic) and 1070 cm$^{-1}$(Si—O—) and nmr spectrum; 7.1 ppm (m,4H); 5.9 and 5.3 ppm (2 broad s,2H); 1.8 ppm (s,3H); 0.0 ppm (broad s,45H).

EXAMPLE 4

Synthesis of trimethylsiloxy-dimethylsilane-(m,p-methacryloxymethyl)phenylethane Trimethylsiloxyl-dimethylsilane(m,p-chloromethyl)-phenylethane was synthesized by the reaction of pentamethyldisiloxane and vinyl benzyl chloride in the presence of chloroplatinic acid. This compound was then reacted with sodium methacrylate in dimethylformamide using procedures similar to those given in Example 2 to form trimethylsiloxyl-dimethylsilane(m-p-methacryloxymethyl)phenylethane in a 50.7% yield. [B.P. 102° C. (0.1 mm)].

The identity of the compound was confirmed by the infrared spectrum; 1730 cm$^{-1}$ (C=O), 1640 cm$^{-1}$ (CH$_2$=), 1615 cm$^1$(aromatic) 1070 cm$^{-1}$(Si—O—) and the nmr spectrum; 7.1 ppm (m,4H); 5.9 and 5.3 ppm (broad s,2H), 5,0 ppm (s,2H), 0 ppm (2s,15H).

EXAMPLE 5

Synthesis of bis (trimethylsiloxy) methylsilane(m,p-methacryloxymethyl)phenylethane Using the procedure set forth in Example 4, bis (trimethylsiloxy) methyl(m,p-methacryloxymethyl)phenylethane was prepared in a yield of 54.7%. [B.P. 104°–124° C. (0.1–0.2 mm)].

The identity of the compound was confirmed by the infrared spectrum; 1730 cm$^{-1}$ (C=0), 1640 cm$^{-1}$ (CH$_2$=), 1070 cm$^{-1}$ (Si—O—) and the nmr spectrum; 7.1 ppm (m,4H); 5.9 and 5.4 ppm (2 broad S,5H), 5.0 ppm (s,2H), 1.8 ppm (s,3H), 0 ppm (2s,21H).

EXAMPLE 6

Synthesis of Tris (trimethylsiloxy) silane(m,p-3-N-methacryloxymethylureido-1-N-methyl)phenylethane Tris (trimethylsiloxy) silane(m,p-azidomethyl)phenyl ethane was prepared by the reaction of 17.9 g. (40 mmole) with 2.80 g. (44 mmole) of sodium azide in 100 ml of methanol under reflux for four hours. After evaporation and washing with 100 ml of distilled water the residue was extracted three times with 100 ml of distilled water the residue was extracted three times with 100 ml portions of ethyl acetate. The combined extracts were washed twice with 50 ml distilled water each time, dried over anhydrous magnesium sulfate and evaporated in vacuo. The reaction product was obtained in 96.6% yield (17.2 g.), b.p. 120°-125° C. (0.4 mm).

Tris (trimethylsiloxy) silane(m,p-aminomethyl)phenylethane was prepared by the catalytic hydrogenation of tris (trimethylsiloxy) silane(m,p-azidomethyl)phenylethane.

To a Parr hydrogenation apparatus (500 ml capacity) were added, 16.3 g. (36 mmole) of tris (trimethylsiloxy) silane(m,p-azidomethyl)phenylethane, 2.6 g. acetic acid, 250 ml isopropanol and 0.87 g. of 5% palladium/charcoal. A cycle of hydrogenation at 5 psi for 15 min., evacuation and hydrogenation at 5 psi for 15 min. is repeated twice. The reaction mixture is filtered with the aid of Celite and the low boiling organics evaporated. The resulting liquid is treated with a 50:50 mixture of 5% aqueous sodium carbonate:ethyl acetate and the organic layer is then dried over anhydrous sodium sulfate. Vacuum distillation yields 10.8 g. (70.7% yield) of tris (trimethylsiloxy) silane(m,p-aminomethyl) phenylethane, b.p. 145°-155° C. (0.1 mm).

The identity of the compound was confirmed by the infrared spectrum; 3350 cm$^{-1}$ (NH$_2$), 1070 cm$^{-1}$ (Si—O) and nmr spectrum; 7.0 ppm (m,4H), 3.8 ppm (s,2H), 1.6 ppm (s,2H), 0 ppm (s,27H).

Compound tris (trimethylsiloxy) silane(m,p-aminomethyl) phenylethane was then prepared from the reaction of tris (trimethylsiloxy) silane(m,p-aminomethyl) phenylethane with isocyanoethyl methacrylate. Compound tris (trimethylsiloxy) silane(m,p-aminomethyl)phenylethane (22.0 g., 51 mmole) was reacted with 10.6 g. (68 mmole) of isocyanoethyl methacrylate in 110 ml methylene chloride in the presence of 2.5-diphenyl-p-benzoquinone as an inhibitor. The isocyanoethyl methacrylate is added dropwise over a period of 30 minutes with stirring while the reaction mixture is cooled by an ice bath. At the end of this time the ice bath was removed and the reaction proceeded at room temperature for an additional 5½ hours. Concentrated ammonium hydroxide (2 ml) is then added. The organic layer is then washed with 40 ml distilled water three times and dried over anhydrous magnesium sulfate. Silica gel column separation with ethyl acetate-hexane as the eluent yielded 19.4 g. (65.0%) of tris (trimethylsiloxy) silane(m,p-3-N-methacryloxymethylureido-1-N-methyl)phenylethane.

The identity of the compound was confirmed by the infrared spectrum; 3380 cm$^{-1}$ (NH), 1730 cm$^{-1}$ (C=O), 1580 cm$^{-1}$ (NHCO), 1070 cm$^{-1}$ (—Si—O) and the nmr spectrum; 7.0 ppm (m,4H), 5.8 and 5.3 ppm (2s,2H), 4.8 ppm (m,2H), 4.1 ppm (m,4H), 3.3 ppm (5,2H), 1.8 ppm (s,3H), 0 ppm (s,27H).

EXAMPLE 7

Synthesis of tris (trimethylsiloxy) silane(m,p-N-methacrylaminomethyl)phenylethane Methacryloyl chloride (2.92 g., 28 mmole) is added dropwise over a period of thirty minutes to a solution of 10.0 g. (23 mmole) of compound tris (trimethylsiloxy) silane(m,p-aminomethyl)phenylethane and 2.83 g. (28 mmole) triethylamine in 100 ml of chloroform on an ice bath. A trace amount of 2,5-diphenyl-p-benzoquinone is added as an inhibitor. After the addition of methacryloyl chloride is complete, the ice bath is removed and the reaction continued for a total of six hours. Concentrated ammonium hydroxide (2 ml) is then added. The organic layer is then washed with 40 ml distilled water three times and dried over anhydrous magnesium sulfate. Vacuum distillation was then employed to obtain a 38% yield of tris (trimethylsiloxy) silane(m,p-N-methacrylaminomethyl)phenylethane [b.p. 170°-175° C. (0.15 mm)].

The identity of the compound was confirmed by the infrared spectrum; 3350 cm$^{-1}$ (NH), 1670 and 1640 cm$^{-1}$ (NHCO), 1070 cm$^{-1}$ (SI—O—) and nmr spectrum; 7.0 ppm (m,4H), 6.0 ppm (broad, 1H), 5.5 and 5.2 ppm (2 broad s,2H), 4.3 ppm (2s,2H), 1.8 ppm (s,3H), 0 ppm (s,27H).

EXAMPLES 8 THROUGH 10

Using the reactions described in Examples 1 through 7, the monomers shown in Table I were prepared:

TABLE I

| Example # | Monomer | nmr data |
|---|---|---|
| 8 | bis (trimethylsiloxy) methylsilane-m,p-N—methacryloylaminomethyl)phenylethane | 7.1 ppm (m,4H)<br>5.6 & 5.3 ppm (2s,2H) |
| 9 | bis (trimethylsiloxy) methylsilane(m,p-3-N—methacryloxyethylureido-1-N—methyl) phenylethane | 7.0 ppm (m,4H)<br>6.0 & 5.5 ppm (2s,2H)<br>4.8 (Broad D$_2$O exchangable)<br>4.2 & 4.1 ppm (2t,4H)<br>3.3 ppm (t,2H)<br>0 ppm (2s,21H) |
| 10 | tris (pentamethyldisiloxy) silane(m,p-3-N—methacryloxyethylureido-1-N—methyl) phenylethane | 7.0 ppm (m,4H)<br>5.9 & 5.7 ppm (2 broad s,2H)<br>1.8 ppm (s,3H) |

EXAMPLES 11 THROUGH 14

Copolymer Films

Films of the copolymers listed in Table II were prepared between (4×4 in.) glass plates. The glass plates were pretreated with dimethyldichlorosilane and hydrolyzed to silanize the surface. Masking tape is placed around the edges of a glass plate to control the film thickness (target thickness was usually 0.1 mm). The monomer mix was placed on a glass plate, the two plates secured together by means of a metal clip and the assembly placed in an oven at 50° C. for one and one half hour. At the end of this time the glass plate assembly was heated to 90° C. for an additional 90 minutes. The think film was then removed from the glass plate assembly and stored in distilled water (phosphate buffer, pH 7.4). For all of the copolymers listed in Table II, 1.0 weight % of USP 245 (2,5-dimethyl-2,5-diperoxy-2'-ethylhexoate hexane) was added.

The composition of each copolymer in mole percent is: siloxane monomer 16.2%, methyl methacrylate 76.9%, methacrylic acid 5.4% and ethylene glycol dimethacrylate 1.5%.

Oxygen permeability (DK) was measured in a water/water cell using an $O_2$ Permeometer ™ Model 101T. The units of DK are $cm^2/sec$ $(mlO_2/ml\ mmHg) \times 10^{-11}$.

TABLE II

| Example # | Copolymer based on | DK |
|---|---|---|
| 11 | tris (pentamethyl disiloxy) silane-m,p-methacryloyloxymethyl phenylethane | 54 |
| 12 | tris (trimethylsiloxy) silane -m,p-methacryloxymethyl phenylethane | 18 |
| 13 | pentamethyldisiloxy-m,p-methacryloxymethyl phenylethane | 8 |
| 14 | bis (trimethylsiloxy) methyl-m,p-methacryloyloxymethyl phenylethane | 2.4 |

EXAMPLE 15

Copolymerization of tris (trimethylsiloxy) silane(m,p-methacryloxymethyl)phenylethane with methyl methacrylate and methacrylic acid Tris (trimethylsiloxy) silane(m,p-methacryloxymethyl) phenylethane 3.84 g. was added to a clean, dry 20 ml glass, screw top test tube along with 3.62 g. methyl methacrylate, 0.39 g. methacrylic acid, 0.16 g. ethyleneglycol dimethacrylate and 0.09 g. USP 245. After degassing with Argon the tube was capped and placed in an oil bath at 50° C. for one hour and then at 70° C. for 72 hours. It was then carried through an annealing cycle at 120° C. A hard, transparent button was obtained that could be machined to a contact lens using standard lathing and polishing techniques. The contact lens thus obtained has a DK of 18.

The following table summarizes some of the monomers which have been or can be prepared in accordance with the invention.

TABLE III

| Compound Name | A | R | X | Y | Z | n |
|---|---|---|---|---|---|---|
| tris(trimethylsiloxy)-silane-(m,p-methacryloxymethyl)-phenylethane | Ester | Methyl | —OSi(CH₃)₃ | * | —CH₃ | 1 |
| tris(pentamethyl disiloxyl silane-(m,p-methacryloxymethyl)phenylethane | Ester | Methyl | —OSi(CH₃)₂OSi(CH₃)₃ | * | —OSi(CH₃)₃ | 1 |
| tris(trimethylsiloxy)-silane-(m,p-N—methacrylaminomethyl)phenylethane | Amide | Methyl | —OSi(CH₃)₃ | * | —CH₃ | 1 |
| bis(trimethylsiloxy)methyl-silane-(m,p-N—methacrylaminomethyl)phenylethane | Amide | Methyl | —CH₃ | OSi(CH₃)₃ | —CH₃ | 1 |
| bis(trimethylsiloxy)methyl-silane-(m,p-methacryloxymethyl)phenylethane | Ester | Methyl | —CH₃ | OSi(CH₃)₃ | —CH₃ | 1 |
| trimethylsiloxy-dimethyl-silane-(m,p-methacryloxymethyl)phenylethane | Ester | Methyl | —CH₃ | * | —CH₃ | 1 |
| tris(pentamethyl disiloxyl silane-(m,p-3-N—methacryloxymethylureido-1-N—methyl)-phenylethane | Urea, m = 2 | Methyl | —OSi(CH₃)₂OSi(CH₃)₃ | * | —OSi(CH₃)₃ | 1 |
| tris(trimethylsiloxy)-silane-(m,p-3-N—methacryloxymethylureido-1-N—methyl)-phenylethane | Urea, m-2 | Methyl | —OSi(CH₃)₃ | * | —CH₃ | 1 |
| bis(trimethylsiloxy)methyl-silane-(m,p-3-N—methacryloxymethylureido-1-N—methyl)-phenylethane | Urea, m = 2 | Methyl | —CH₃ | OSi(CH₃)₃ | —CH₃ | 1 |

*Y and X are the same.

Those monomers prepared in examples 2, 3 and 6, which are also shown in Table III, are preferred.

What is claimed is:

1. A siloxane monomer having the formula:

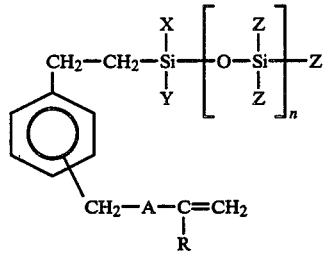

wherein,
(1) "A" is selected from the group consisting of:

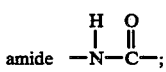

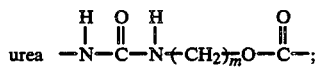

where m is a number and is from 2–4;
(2) R is hydrogen or methyl;
(3) X and Y are selected from the group consisting of $C_1$ to $C_5$ alkyl groups, phenyl groups and W groups;
(4) W is a group of the structure

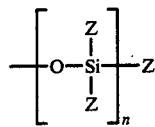

(5) Z is selected from the group consisting of $C_1$ to $C_5$ alkyl groups and phenyl groups; and (6) n is an integer from zero to five.

2. The siloxane monomer of claim 1 wherein A is an ester group.

3. The siloxane monomer of claim 1 wherein A is an amide group.

4. The siloxane monomer of claim 1 wherein A is a ureido group.

5. The siloxane of claim 1 wherein X and Y are methyl.

6. The siloxane of claim 1 wherein W is trimethylsiloxyl.

7. The siloxane of claim 1 wherein W is pentamethyldisiloxyl.

8. The monomer of claim 1 wherein: A is an ester group, R is methyl, X and Y are: $-OSi(Ch_3)_3$, Z is methyl and R is 1.

* * * * *